(12) United States Patent
Püntener et al.

(10) Patent No.: US 6,437,118 B1
(45) Date of Patent: Aug. 20, 2002

(54) VINYLATING OF PYRIMIDINE DERIVATIVES

(75) Inventors: Kurt Püntener, Basel; Michelangelo Scalone, Birsfelden, both of (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 09/577,708

(22) Filed: May 23, 2000

(30) Foreign Application Priority Data

May 26, 1999 (EP) .............................. 99110222

(51) Int. Cl.⁷ ............................................ C07H 19/067
(52) U.S. Cl. ................................ 536/27.11; 536/28.52; 544/242
(58) Field of Search ........................... 536/27.11, 28.52; 544/242

(56) References Cited

U.S. PATENT DOCUMENTS

| | | | |
|---|---|---|---|
| 5,428,149 A | 6/1995 | Eaton | |
| 5,576,429 A | 11/1996 | Johansson et al. | |
| 6,005,098 A | 12/1999 | Hattori et al. | 536/28.52 |
| 6,114,520 A * | 9/2000 | Hattori et al. | 536/28.5 |
| 6,211,166 B1 * | 4/2001 | Hattori et al. | 514/49 |

FOREIGN PATENT DOCUMENTS

| | | |
|---|---|---|
| EP | 103 375 | 4/1984 |
| EP | 0 882 734 A2 | 12/1998 |
| WO | WO 97 44326 A1 | 11/1997 |

OTHER PUBLICATIONS

Darses et al., "Potassium Vinyltrifluoroborate: A Stable and Efficient Vinylating Agent of Arenediazonoium Salts Using Palladium Catalysts," *Tetrahedron Letters*, 39, 5045–5048 (1998).*
Hunt et al., "Heck versus Suzuki Palladium Catalyzed Cross–Coupling of a Vinylboronate Ester with Aryl Halides," *Tetrahedron Letters*, 34(22), 3599–3602 (1995).*
Perlman et al., "Nucleosides. 133. Synthesis of 5–Alkenyl–1–(2–deoxy–2–fluoro–α–D–arabinofuranosyl) cytosines and Ralated Pyrimidine Nucleosides as Potential Antiviral Agents," *Journal of Medicinal Chemistry*, 28(6), 741–748 (1985).*

* cited by examiner

*Primary Examiner*—Johann Richter
*Assistant Examiner*—L. Eric Crane
(74) *Attorney, Agent, or Firm*—George W. Johnston; Robert A. Silverman

(57) ABSTRACT

The invention relates to a process for the preparation of vinyl pyrimidines of the formula I

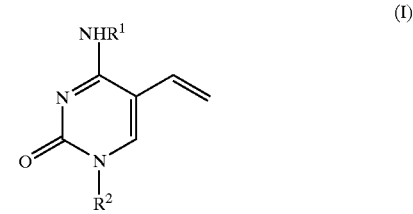

wherein $R^1$ is hydrogen or a carboxylic ester group, and $R^2$ is hydrogen or a group of the formula (a)

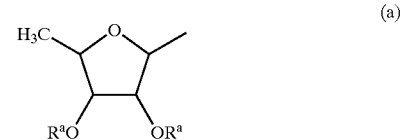

wherein $R^a$ is hydrogen, a protecting group or a group easily hydrolyzable under physiological conditions, by reacting a compound of the formula II

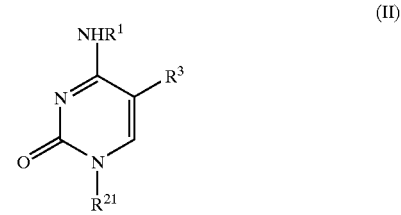

wherein $R^{21}$ is hydrogen or a group (a) wherein hydroxy groups are optionally protected, $R^3$ is bromo, chloro or iodo, and $R^1$ is as above, with a vinyl borane compound in the presence of a Pd complex and a base, and optionally, further reacting a product of formula I wherein $R^2$ is hydrogen with a compound of the formula IV

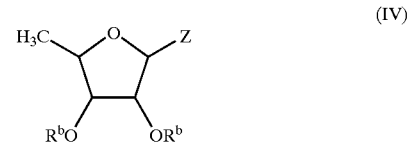

wherein $R^b$ is a hydroxy protecting group and Z is a leaving group, in the presence of a Lewis acid catalyst.

16 Claims, No Drawings

VINYLATING OF PYRIMIDINE DERIVATIVES

FIELD OF THE INVENTION

The present invention is concerned with a process for the preparation of vinyl pyrimidine derivatives. More particularly, the present invention is concerned with a process for vinylating pyrimidine derivatives, such as cytosine and cytidine derivatives.

BACKGROUND

5'-Deoxy-5-vinylcytidine derivatives are of interest in the therapy of cancer, see International application PCT/EP99/00710. However, the preparation of these compounds as disclosed in said International application does not proceed in satisfactory yield and involves the use of tri-n-butyl vinyl stannane, a costly and toxic reagent which also gives rise to tedious purification of the final product and problems in disposing of toxic waste.

In accordance with the present invention it has been found that the vinylation of pyrimidine derivatives can be accomplished with the use of vinyl boranes. The process in accordance with the present invention proceeds in superior yield and does not provide the economic and environmental problems of the prior art process.

SUMMARY OF THE INVENTION

In one aspect, the present invention is concerned with a process for the preparation of compounds of the formula I

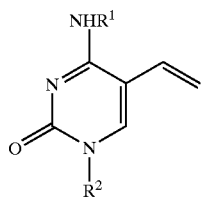

(I)

wherein $R^1$ is hydrogen or a carboxylic ester group, and $R^2$ is hydrogen or a group of the formula (a)

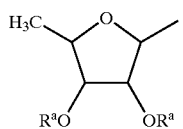

(a)

wherein $R^a$ is hydrogen, a hydroxy protecting group or a group easily hydrolyzable under physiological conditions, which comprises reacting a compound of the formula II

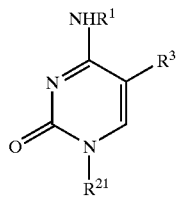

(II)

wherein $R^{21}$ is hydrogen or a group (a) wherein hydroxy groups are optionally protected, $R^3$ is bromo, chloro or iodo, and $R^1$ is as above, with a vinyl borane compound of the formula IIIa or IIIb $(CH_2=CH)_n B(R^6)_{3-n} L_m$ (IIIa)

$[(CH_2=CH)_p B(R^6)_{4-p}] X^+$ (IIIb)

wherein n is 1, 2 or 3;

m is 0 or 1;

$R^6$ is hydrogen, halogen, alkyl, cycloalkyl, alkoxy, cycloalkoxy, hydroxy or aryl, and wherein, if more than one group $R^6$ is present, these groups may be different from each other, or two groups $R^6$ may, together with —A—$(CH_2)_q$—Y—$(CH_2)_r$—A—, form a carbocyclic or heterocyclic ring wherein A and Y are $CH_2$ or NH or O and q and r are an integer from 0–4, or two groups $R^6$ may also form a catechol moiety

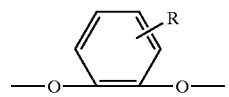

in which R is hydrogen or lower alkyl;

L is an amine, a Schiff base or an ether;

p is 1, 2, 3 or 4;

$X^+$ is a cation;

in the presence of a Pd complex and a base, and, if desired, removing any protecting group from a compound of formula I wherein $R^2$ is a group (a).

The compounds of formula I are known (for example, see U.S. patent application Ser. No. 09/484,174, filed Jan. 14, 2000 and U.S. Pat. No. 6,005,098, both herein incorporated by reference).

DETAILED DESCRIPTION OF THE INVENTION

As used herein the term "carboxylic ester group" preferably denotes a group —$COOR^4$ wherein $R^4$ is —$(CH_2)_n$-cycloalkyl [wherein cycloalkyl consists of 3 to 6 carbon atoms, n is an integer from 0 to 4], heteroaryl-(lower-alkyl), (lower-alkoxy)-(lower-alkyl), aryloxy-(lower-alkyl), aralkyloxy-(lower-alkyl), (lower-alkylthio)-(lower-alkyl), arylthio-(lower-alkyl), aralkylthio-(lower-alkyl), oxo-(lower-alkyl), acylamino-(lower-alkyl), cyclic amino-(lower-alkyl), (2-oxocyclic amino)-(lower-alkyl) wherein the alkylene chain may be further substituted with one or two lower-alkyl group(s). The term "lower" means groups containing up to and including 5 carbon atoms. "Acyl" denotes aliphatic or aromatic carboxylic moieties such as lower alkanoyl or benzoyl.

Examples of the group —$(CH_2)_n$-cycloalkyl are cyclobutyl, cyclopropylmethyl and cyclopentylmethyl. Examples of heteroaryl-(lower-alkyl) are pyridin-3-ylmethyl, pyridin-2-ylmethyl, pyridin-4-ylmethyl, 1-(pyridin-4-yl)ethyl, (6-methylpyridin-2-yl)methyl and 1-(6-ethylpyridin-2-yl)propyl. Examples of (lower-alkoxy)-(lower-alkyl) are 2-methoxy-ethyl, 2-thoxyethyl, 3-methoxypropyl, 3-ethoxypropyl, 3-methoxy-3-methylbutyl, 3-ethoxy-3-methylbutyl, 3-methoxy-2,2-dimethylpropyl, 3-ethoxy-2,2-dimethylpropyl, 2-ethyl-2-methoxymethylbutyl and 2-ethyl-2-ethoxymethylbutyl. Examples of aryloxy-(lower-alkyl) are 2-phenoxyethyl, 1-phenoxypropyl and 3-phenoxypropyl. Examples of aralkyloxy-(lower-alkyl) are 2-benzyloxyethyl, 3-benzyloxypropyl and 5-benzyloxypentyl. Examples of (lower-alkylthio)-(lower-alkyl) are 2-methylthioethyl, 2-ethylthioethyl, 3-methylthiopropyl and 3-ethylthiopropyl.

Examples of arylthio-(lower-alkyl) are 2-phenylthioethyl and 3-phenylthiopropyl. Examples of aralkylthio-(lower-alkyl) are 2-(benzylthio)ethyl and 3-(benzylthio)propyl. Examples of oxo-(lower-alkyl) are 4-oxopentyl, 3-oxo-2-methylbutyl and 2-oxobutyl. Examples of acylamino-(lower-alkyl) are 2-(acetylamino)-ethoxy, 3-(acetylamino)propyl, 3-(n-propionylamino)propyl and 3-(benzoylamino)propyl. Examples of cyclic amino-(lower-alkyl) are 2-morpholinoethyl, 3-morpholinopropyl, 2-piperidinoethyl, 3-piperidinopropyl, 2-pyrrolidinoethyl and 3-pyrrolidinopropyl. Examples of (2-oxocyclic amino)-(lower-alkyl) are 2-oxopyrrolidin-1-ylethyl and 2-oxopiperidin-1-ylethyl. Preferably, $R^1$ is hydrogen.

The term "a group easily hydrolyzable under physiological conditions" preferably means acetyl, propionyl, benzoyl, toluoyl, glycyl, alanyl, β-alanyl, valyl or lysyl. Examples of hydroxy protecting groups are acetyl, benzoyl, trimethylsilyl and tert.butyldimethylsilyl. Preferably, $R^a$ is acetyl which serves as physiologically hydrolyzable and protecting group as well.

Preferred vinyl boranes of formula IIIa and IIIb are those of the formulae

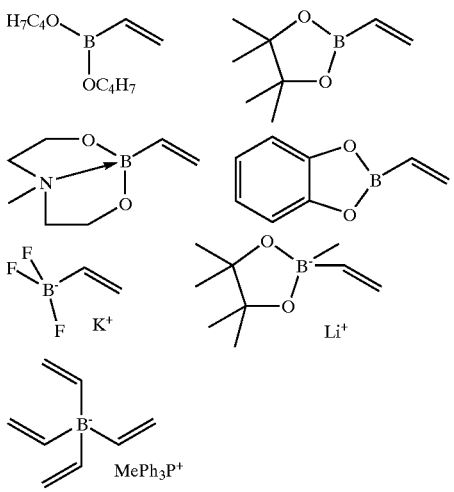

The preferred vinyl boranes are potassium vinyl trifluoroborate and 4,4,5,5-tetramethyl-2-vinyl-1,3,2-dioxaborolan.

The Pd complex used as a catalyst in the vinylation reaction according to the invention can be a neutral Pd(0) or Pd(II) complex or a cationic Pd(II) complex. Examples of such Pd complexes are $Pd(OAc)_2$, $Pd(OAc)_2/dppf$, $Pd(OAc)_2/dppp$, $Pddba_2$, $Pd_2dba_3$, $Pd_2dba_3/PPh_3$, $Pd_2dba_3/P(O.Tol)_3$, $Pd_2dba_3/P(mTol)_3$, $Pd_2dba_3/P(2-Furyl)_3$, $PdCl_2dppf$, $PdCl_2(PPh_3)_2$, $PdCl_2dppe$, $PdCl_2(NCMe)_2$, $PdCl_2(NCMe)_2/(R)$-BIPHEMP, $Pd_2Cl_2(\pi\text{-allyl})_2$, $Pd(PPh_3)_4$, $[Pd(NCMe)_4](BF_4)_2$, Pd/C, and Bedford's catalyst, wherein the structures of the phosphines present in the above recited catalysts are as shown below:

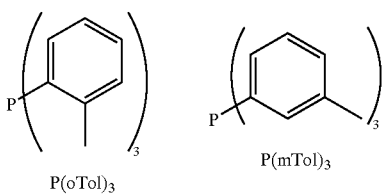

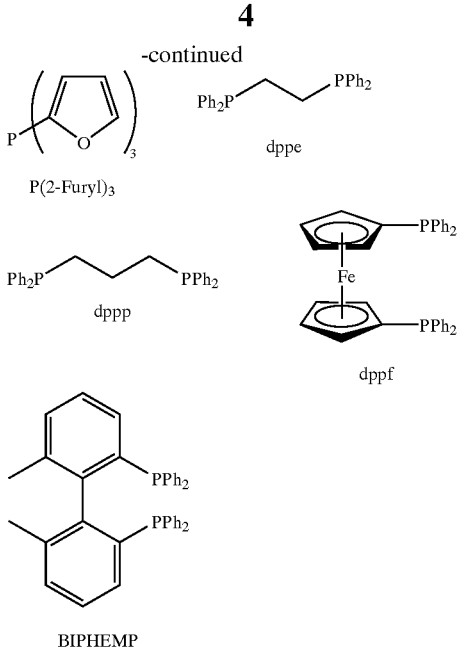

BIPHEMP

As used above, the term "Ph" means phenyl and "dba" means dibenzylideneacetone.

The preferred catalysts for the vinylation reaction are $PdCl_2(dppf)$ and $Pd_2dba_3/PPh_3$. All the Pd catalysts are known from literature and are commercially available, e.g. from Fluka, Buchs S G, Switzerland, or Strem Chemicals, Kehl, Germany, or can be prepared in situ from commercially available components. The synthesis of (R)-BIPHEMP is described in EP 104 375.

Suitably, the vinylation reaction according to the invention is carried out in the presence of a base. The base can be an organic base such as a tertiary, secondary and primary amine, e.g. triethyl amine, diisopropyl ethylamine, tert-butyl amine, pyrrolidine, pyridine, alkali alcoholates such as potassium ethylate, or a salt of a carboxylic acid such as sodium acetate; or an inorganic base e.g., a carbonate such as sodium carbonate and potassium hydrogen carbonate, or hydroxide, or salt of phosphoric acid, sulfuric acid and fluoric acid such as $K_3PO_4$ and $CsF_2$. Preferred bases are triethyl amine and tributyl amine.

Suitably, the vinylation is carried out in the presence of a solvent such as water, lower aliphatic alcohols, e.g. methanol, ethanol, n-propanol, iso-propanol or n-butanol, nitrites, e.g. acetonitrile, hydrocarbons such as toluene, halogenated hydrocarbons, e.g. methylene chloride, esters, e.g., ethyl acetate, amides, e.g. dimethylformamide, pyridine or N-methyl pyridine, ethers, e.g. tetrahydrofuran or dioxan, urethanes, e.g. TMU, sulfoxides, e.g. DMSO or mixtures thereof. The preferred solvent for the vinylation reaction is ethanol or methanol.

The reaction temperature is not critical and can be, e.g., within the range of 0–200° C., preferably 40–150° C. The amount of catalyst is not narrowly critical. For example, 1–10 000 moles, preferably 10–200 moles of substrate can be used per mol of catalyst. The amount of vinyl borane is preferably 1–10 equivalents; and the amount of base is preferably 0–10 equivalents, more preferably 0–1.5 equivalents.

The compounds of formula II are known (for example, see U.S. patent application Ser. No. 09/484,174, filed Jan. 14, 2000 and U.S. Pat. No. 6,005,098), or can be prepared by conventional methods from known starting materials. The compounds of formulas IIIa and IIIb are known (for example, see Darses et al., Tetrahedron Letters 39 (1998) 5045–5048, incorporated herein by reference), or can be prepared by conventional methods from known starting materials.

In a preferred aspect, the invention is concerned with the vinylation of a compound of formula II wherein $R^1$ is hydrogen and $R^2$ is a group (a) as defined above. According to this preferred aspect, the reaction is most suitably carried out using a compound of formula II wherein $R^3$ is bromo and the vinyl borane compound is potassium vinyltrifluoroborate. Furthermore, the reaction according to this preferred aspect is most suitably carried out using $PdCl_2(dppf)$ as the catalyst.

In another aspect, the invention is concerned with the vinylation of a compound of formula II wherein $R^1$ is hydrogen and $R^2$ is hydrogen. According to this aspect, the reaction is most suitably carried out using a compound of formula II wherein $R^3$ is iodo and the vinyl borane compound is 4,4,5,5-tetramethyl-2-vinyl-1,3,2-dioxaborolan. Furthermore, the reaction according to this preferred aspect is most suitably carried out using $Pd_2dba_3/PPh_3$ as the catalyst.

In another aspect of the invention, the invention is concerned with the further conversion of a compound of formula I wherein $R^2$ is hydrogen by reaction with a compound the formula IV

(IV)

wherein $R^b$ is a hydroxy protecting group and Z is a leaving group, in the presence of a Lewis acid catalyst to yield a compound of formula I wherein $R^2$ is a group (a), whereupon, if desired, a hydroxy protecting group $R^b$ is removed. The leaving group can be any leaving group that's is customary in such coupling reactions, for example, an acyl group such as acetyl or benzoyl or halogen, such as chloro. Preferably, the leaving group is acetyl. Specific examples of the compound represented by the general formula (IV) include the known 5-deoxy-1,2,3-tri-O-acetyl-D-ribofuranoside, 5-deoxy-1,2,3-tri-O-benzoyl-D-ribofuranoside, and the like.

Examples of Lewis acids for use in this reaction are tin(IV) chloride, titanium(IV) chloride, trifluoromethane sulfonic acid and the like. This coupling reaction can be carried out in a solvent such as acetonitrile, dichloromethane, chloroform, 1,2-dichloroethane, nitromethane, toluene and the like, at a temperature between 0 and 50° C.

In the reaction product of the formula I a hydroxy protecting group can be removed in a manner known per se, such as base hydrolysis.

The invention is illustrated further by the Examples which follow.

A. Preparation of the Starting Compounds

EXAMPLE 1

74.9 g of 5-bromocytosine (0.394 mol), 1.03 g of ammonium sulfate (0.008 mol) and 86.5 ml of hexamethyldisilazane (0.415 mol) in 700 ml of toluene were heated to reflux for 4 hours. After concentrating the reaction solution the residue was dissolved in 1.41 of methylene chloride and 286.7 g of a 39.4% $CH_2Cl_2$ solution of 5-deoxy-1,2,3-tri-O-acetyl-D-ribofuranoside (0.433 mol) were added thereto. Then, 51.0 ml of stannous tetrachloride (0.433 mol) were added dropwise within 20 minutes and the reaction mixture was continued to stir for 4 hours. After the addition of 180 g of sodium bicarbonate 78 ml of water were added. After stirring for 2 hours the mixture was filtered. The filtrate was washed with water, dried over magnesium sulfate, and evaporated to dryness. The residue was suspended in 800 ml of isopropanol, the suspension concentrated to half the volume, filtered and the solids washed with isopropanol and then with tert-butylmethyl ether. Subsequently, the crude product was suspended in 250 ml of tert-butylmethyl ether, filtered and dried. There were isolated 140.4 g (91.3%, 99.7 HPLC area-%) of 4-amino-5-bromo-1-(2,3-di-O-acetyl-5-deoxy-beta-D-ribofuranosyl)-1H-pyrimidin-2-one as a white powder; mp. 219–220° C. (dec.). MS (ISP-MS): (m/z) 390 [M+H]$^+$. $^1$H-NMR (250 MHz, CDCl$_3$): 1.46 (3H, d, J=6.3), 2.09 (3H, s), 2.11 (3H, s), 4.25 (1H, quint., J=6.3), 5.01 (1H, t, J=6.0), 5.33 (1H, t, J=5.7), 5.6–5.8 (1H, br), 5.99 (1H, d, J=4.1), 7.59 (1H, s), 7.6–7.8 (1H, br).

EXAMPLE 2

In analogy to Example 1, 29.1 g of 5-bromocytosine (0.153 mol) were reacted with 111.1 g of a 39.4% $CH_2Cl_2$ solution of 5-deoxy-1,2,3-tri-O-acetyl-D-ribofuranoside (0.168 mol) using 19 ml of TiCl$_4$ (0.168 mol) instead of SnCl$_4$. There were obtained 39.0 g (65%, 98.8 HPLC area-%) of 4-amino-5-bromo-1-(2,3-di-O-acetyl-5-deoxy-beta-D-ribofuranosyl)-1H-pyrimidin-2-one, m.p. 223° C. (dec.). MS- and $^1$H-NMR spektra were in agreement with those of the product obtained in Example 1.

EXAMPLE 3

30.2 g of 5-bromocytosine (0.159 mol), 14 μl of trifluoromethane sulfonic acid and 36.0 ml of hexamethyldisilazane (0.173 mol) in 300 ml of acetonitrile were heated to reflux for 1 hour. Then, a solution of 45.5 g of crystalline 5-deoxy-1,2,3-tri-O-acetyl-D-ribofuranoside in 45 ml of acetonitrile and 8.3 ml of trifluoromethane sulfonic acid was added and the mixture stirred for 23 hours at 50° C. The solvent was then evaporated and the residue dissolved in 700 ml of methylenechloride. The $CH_2Cl_2$ solution was washed with water, dried over magnesium sulfate and evaporated to dryness. The residue was suspended in 300 ml of isopropanol, concentrated to half the volume, filtered and the solid washed with isopropanol and then with tert.butylmethyl ether. There were obtained 43.0 g (70%, 98.8 HPLC area-%) of 4-amino-5-bromo-1-(2,3-di-O-acetyl-5-deoxy-beta-D-ribofuranosyl)-1H-pyrimidin-2-one, m.p. 196–197° C. (dec.). MS- and $^1$H-NMR were in agreement with those of the product obtained in Example 1.

EXAMPLE 4

In analogy to Example 2, 6.68 g of 5-chlorocytosine (45.9 mmol) were reacted with 13.14 g of a 35% $CH_2Cl_2$solution of 5-deoxy-1,2,3-tri-O-acetyl-D-ribofuranoside (50.5 mmol). There as obtained 4-amino-5-chloro-1-(2,3-di-O-acetyl-5-deoxy-beta-D-ribofuranosyl)-1H-pyrimidin-2-one in yield of 80% (13 g) as white crystals, m.p. 226–227° C. (dec.). MS (ISP-MS): (m/z) 346 [M+H]$^+$. $^1$H-NMR (250 MHz, CDCl$_3$): 1.46 (3H, d, J=6.1), 2.09 (3H, s), 211 (3H, s), 4.25 (1H, quint., J=6.4), 5.00 (1H, t, J=6.1), 5.34 (1H, t, J=5.7), 5.6–5.8 (1H, br), 5.97 (1H, d, J=4.0), 7.50 (1H, s), 8.2–8.4 (1H, br).

B. Process of the Invention

EXAMPLE 5

0.665 g of dichlorobis(acetonitril) palladium(II) (2.56 mmol) and 1.421 g of dppf (2.56 mmol) were dissolved in 1 l of ethanol and stirred for 30 minutes at room temperature. Then, 100.00 g of 4-amino-5-bromo-1-(2,3-di-O-acetyl-5-deoxy-beta-D-ribofuranosyl)-1H-pyrimidin-2-one (0.256 mol), 51.49 g of potassium trifluorovinylborate (0.384 mol) and 36 ml of triethylamine (0.256 mol) were added and the suspension heated to reflux for 4¼ hours. The mixture was cooled, filtered, the solids washed with ethanol and the combined filtrates evaporated to dryness. The residue was heated to reflux in 2 l of ethanol. The hot suspension was filtered, the filtrate washed with water and dried over magnesium sulfate. On concentrating to ca. 200 ml the crude product precipitates as white crystals. (54.75 g, 63.3%). From the mother liquor, an additional 1.65 g of (1.9%) product were isolated. The combined crystallisates (56.40 g) were heated to reflux in the presence of 2.82 g charcoal and 1.6 l of ethylacetate. After filtration the solution was concentrated to ca. 150 ml and the crystals that precipitated isolated. There were obtained 52.31 g (60.5%) of 4-amino-1-(2,3-di-O-acetyl-5-deoxy-beta-D-ribofuranosyl)-5-vinyl-1H-pyrimidin-2-one, m.p. 198–199° C., MS (ISP-MS): (m/z) 338 [M+H]$^+$. $^1$H-NMR (250 MHz, CDCl$_3$): 1.45 (3H, d, J=6.5), 2.08 (3H, s), 2.10 (3H, s), 4.23 (1H, quint., J=6.5), 5.04 (1H, t, J=6.2), 5.33 (1H, d, J=11.1), 5.39 (1H, dd, J=5.7, 4.2), 5.47 (1H, d, J=17.3), 6.01 (1H, d, J=4.2), 6.36 (1H, q, J=17.3, 11.1), 7.38 (1H, s), 8.0–8.5 (2H, br).

EXAMPLE 6

In analogy to Example 5 the coupling of 4-amino-5-bromo-1-(2,3-di-O-acetyl-5-deoxy-beta-D-ribofuranosyl)-1H-pyrimidin-2-one and potassium trifluorovinylborate in 0.25–5.0 g scale was carried out with the bases shown in Table 1

TABLE 1

| Example | Base | % Conversion[1] after 4 h | Yield[2] HPLC Fl.-% |
|---|---|---|---|
| 6.1 | Et(iPr)$_2$N | 98 | 94 |
| 6.2 | Pyrrolidine | 98 | 90 |
| 6.3 | tBuNH$_2$ | 99.9 | 97 |
| 6.4 | KOEt | 99.9 | 72[3] |
| 6.5 | Na$_2$CO$_3$ | 83 | 57 |
| 6.6 | KHCO$_3$ | 68 | 66 |
| 6.7 | NaOAc | 57 | 55 |

[1] percentage of starting material that was converted in the reaction
[2] of 2,3-diacetate
[3] of deacetylated product

EXAMPLE 7

In analogy to Example 5 the coupling of 4-amino-5-bromo-1-(2,3-di-O-acetyl-5-deoxy-beta-D-ribofuranosyl)-1H-pyrimidin-2-one and potassium trifluorovinylborate in 0.25–5.0 g scale was carried out with the catalysts shown in Table 2

TABLE 2

| Example | Catalyst | % Conversion after 4 h | Yield HPLC Fl.-% |
|---|---|---|---|
| 7.1 | PdCl$_2$(dppf) | >99.9 | 97 |
| 7.2 | PdCl$_2$(NCMe)$_2$ | 72 | 61 |
| 7.3 | Pd(OAc)$_2$ | 62 | 52 |
| 7.4 | PdCl$_2$(dppe) | 46 | 41 |
| 7.5 | PdCl$_2$((R)- BIPHEMP) | 40 | 34 |
| 7.6 | Bedford's cat.[1] | 44 | 36 |

EXAMPLE 8

In analogy to Example 5 the coupling of 4-amino-5-bromo-1-(2,3-di-O-acetyl-5-deoxy-beta-D-ribofuranosyl)-1H-pyrimidin-2-one and potassium trifluorovinylborate in 0.25–5.0 g scale was carried out with the solvents and at temperatures shown in Table 3

TABLE 3

| Example | Solvent | Temp. [° C.] | % Conversion after 4 h | Yield HPLC Fl.-% |
|---|---|---|---|---|
| 8.1 | EtOH | 60 | 35 | 31 |
| 8.2 | H$_2$O | 100 | 25 | 11 |
| 8.3 | MeOH | 65 | 95 | 88 |
| 8.4 | nPrOH | 100 | >99.9 | 95 |
| 8.5 | nBuOH | 120 | >99.9 | 95 |
| 8.6 | NCMe | 80 | 74 | 59 |
| 8.7 | DMSO | 100 | 47 | 44 |
| 8.8 | DMF | 100 | 25 | 23 |
| 8.9 | Dioxane | 100 | 49 | 37 |
| 8.10 | Toluene | 100 | 69 | 51 |

EXAMPLE 9

In analogy to Example 5 the coupling was carried out using 280.0 mg of 4-amino-1-(2,3di-O-acetyl-5-deoxy-beta-D-ribofuranosyl)-5-iodo-1H-pyrimidin-2-one(0.64 mmol). After 4 hours the conversion (according to HPLC) was 80% with a content of 39% of 4-amino-1-(2,3-di-O-acetyl-5-deoxy-beta-D-ribofuranosyl)-5-vinyl-1H-pyrimidin-2-one.

EXAMPLE 10

43.4 mg of 4,4,5,5-tetramethyl-2-vinyl-1,3,2-dioxaborolan (0.28 mmol), 100.0 mg of 4-amino-5-bromo-1-(2,3-di-O-acetyl-5-deoxy-beta-D-ribofuranosyl)-1H-pyrimidin-2-one (0.26 mmol), 2.87 mg of Pd(OAc)$_2$ (0.013 mmol) and 77.8 mg of CsF$_2$ (0.512 mmol) in 5 ml of methanol were heated to reflux for 3 hours. After 4 hours the conversion (according to HPLC) was 88% with a content of 34% of 4-amino-1-(2,3-di-O-acetyl-5-deoxy-beta-D ribofuranosyl)-5-vinyl-1H-pyrimidin-2-one.

EXAMPLE 11

177.4 mg of 6-methyl-2-vinyl-1,3,6,2-dioxazaborocan (1.258 mmol), 500.0 mg of 4-amino-1-(2,3-di-O-acetyl-5-deoxy-beta-D-ribofuranosyl)-5-iodo-1H-pyrimidin-2-one (1.14 mmol) and 40.1 mg of PdCl$_2$(PPh$_3$)$_2$ (0.0572 mmol) in 10 ml THF were heated to reflux for 21 hours. After 4 hours the conversion (according to HPLC) was 67% with a content of 32% of 4-amino-1-(2,3-di-O-acetyl-5-deoxy-beta-D-ribofuranosyl)-5-vinyl-1H-pyrimidin-2-one.

EXAMPLE 12

170.0 mg of lithium [2,3-dimethyl-2,3-butanediolato(2-)-O,O']methylvinylborate (0.10 mmol), 280.0 mg of 4-amino-1-(2,3-di-O-acetyl-5-deoxy-beta-D-ribofuranosyl)-5-iodo-1H-pyrimidin-2-one (0.64 mmol) and 7.2 mg of Pd(OAc)$_2$ (0.032 mmol) in 10 ml of ethanol were stirred at room temperature for 30 minutes. After 4 hours the conversion (according to HPLC) was 98% with a content of 36% of 4-amino-1-(2,3-di-O-acetyl-5-deoxy-beta-D-ribofuranosyl)-5-vinyl-1H-pyrimidin-2-one.

EXAMPLE 13

7.24 g of 4,4,5,5-tetramethyl-2-vinyl-1,3,2dioxaborolan (46.4 mmol), 10.00 g of 5-iodocytosine (42.2 mmol), 1.11 g of triphenylphosphine (14.2 mmol), 1.05 g of Pd$_2$dba$_3$·CHCl$_3$ (1.1 mmol) and 15.1 ml tributylamine (63.3 mmol) in 200 ml of methanol were heated to reflux for 28 hours. After cooling the suspension to room temperature the crude product was filtered off and washed with methylene chloride. Crystallisation from boiling methanol gave 3.9 g (61%) of 5-vinylcytosine as white crystals, m.p. >290° C., MS (EI-MS): (m/z) 137 [M+H]$^+$. $^1$H-NMR (250 MHz, D$_6$-DMSO): 5.03 (1H, d, J=11.0), 5.45 (1H, d, J=17.3), 6.52 (1H, dd, J=17.3, 11.0), 6.8–7.2 (3H, br), 7.56 (1H, s).

EXAMPLE 14

In analogy to Example 2, 1.23 g of 5-vinylcytosine (8.62 mmol) were reacted with 7.36 g of a 35% CH$_2$Cl$_2$ solution of 5-deoxy-1,2,3-tri-O-acetyl-D-ribofuranoside (9.90 mmol) using 1.1 ml of TiCl$_4$ (10.0 mmol). The yield of 4-amino-1-(2,3-di-O-acetyl-5-deoxy-beta-D-ribofuranosyl)-5-vinyl-1H-pyrimidin-2-one was 1.00 g (33%, 98.0 HPLC area-%).

The $^1$H-NMR spektrum was in agreement with that of the product obtained in Example 1.

EXAMPLE 15

In analogy to Example 3, 0.81 g of 5-vinylcytosine (5.83 mmol) were reacted with 1.71 g of crystalline 5-deoxy-1,2,3-tri-O-acetyl-D-ribofuranoside (6.55 mmol) using 0.3 ml of trifluoromethane sulfonic acid (3.50 mmol). The yield of 4-amino-1-(2,3-di-O-acetyl-5-deoxy-beta-D-ribofuranosyl)-5-vinyl-1H-pyrimidin-2-one was 1.00 g (33%, 98.0 HPLC area-%).

The $^1$H-NMR spektrum was in agreement with that of the product obtained in Example 1.

We claim:

1. A process for the preparation of a compound of formula I

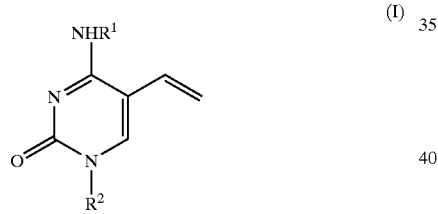

(I)

wherein R$^1$ is hydrogen or COOR$^4$ and R$^4$ is (CH$_2$)$_n$-cycloalkyl wherein cycloalkyl consists of 3 to 6 carbon atoms and n is an integer from 0 to 4, heteroaryl-(lower alkyl), (lower-alkoxy)-(lower alkyl), aryloxy-(lower-alkyl), aralkyloxy-(lower-alkyl), (lower-alkylthio)-(lower-alkyl), arylthio-(lower-alkyl), aralkylthio-(lower-alkyl), oxo-(lower-alkyl), acylamino-(lower-alkyl), cyclic amino-(lower-alkyl), (2-oxocyclic amino)-(lower-alkyl) wherein the alkylene chain is unsubstituted or substituted with one or two lower alkyl groups; and R$^2$ is hydrogen or a group of the formula (a)

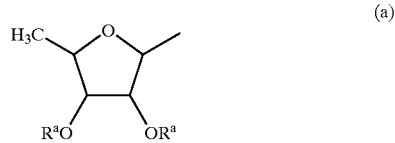

(a)

wherein R$^a$ is hydrogen, a hydroxy protecting group or a group easily hydrolyzable under physiological conditions selected from acetyl, propionyl, benzoyl, toluoyl, glycyl, alanyl, β-alanyl, valyl and lysyl which comprises reacting a compound of the formula II

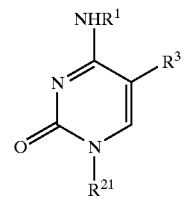

(II)

wherein R$^{21}$ is hydrogen or a group (a) wherein hydroxy groups are unprotected or protected, R$^3$ is bromo, chloro or iodo, and R$^1$ is hydrogen or a carboxylic ester group, with a vinyl borane compound of the formula IIIa or IIIb

(IIIa)

(IIIb)

wherein n is 1, 2 or 3;

m is 0 or 1;

R$^6$ is hydrogen, halogen, alkyl, cycloalkyl, alkoxy, cycloalkoxy, hydroxy or aryl, and wherein, if more than one group R$^6$ is present, these groups may be different from each other, or two groups R$^6$ may, together with —A—(CH$_2$)$_q$—Y—(CH$_2$)$_r$—A—, form a carbocyclic or heterocyclic ring wherein A and Y are CH$_2$ or NH or O and q and r are an integer from 0–4, or two groups R$^6$ may also form a catechol moiety

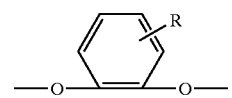

in which

R is hydrogen or lower alkyl;

L is an amine, a Schiff base or an ether;

p is 1, 2, 3 or 4;

X$^+$ is a cation;

in the presence of a Pd complex and a base.

2. A process as in claim 1 wherein R$^2$ is a group (a).

3. A process as in claim 2 wherein R$^3$ is bromo.

4. A process as in claim 3 wherein the vinyl borane compound is potassium vinyltrifluoroborate.

5. A process as in claim 2 wherein the Pd complex is a neutral Pd(0) or Pd(II) complex or a cationic Pd(II) complex.

6. A process as in claim 5 wherein the Pd complex is a neutral Pd(II) complex.

7. A process as in claim 6 wherein the neutral Pd(II) complex is dichloro (1,1'-bis(diphenylphosphino)ferrocene) Pd(II).

8. A process as in claim 1 wherein R$^2$ is hydrogen.

9. A process as in claim 8 wherein R$^3$ is iodo.

10. A process as in claim 9 wherein the vinyl borane compound is 4,4,5,5-tetramethyl-2-vinyl-1,3,2-dioxaborolan.

11. A process as in claim 10 wherein the Pd complex is a neutral Pd(0) complex.

12. A process as in claim 11 wherein the neutral Pd(0) complex is tris(dibenzylideneacetone)-dipalladium(0)/triphenylphosphine.

13. A process as in claim 1 wherein the compound of formula I wherein $R^2$ is hydrogen further comprising reacting the compound of Formula I with a compound of the formula IV

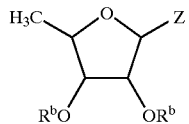

(IV)

wherein $R^b$ is a hydroxy protecting group and Z is a leaving group, in the presence of Lewis acid catalyst, to yield a compound of formula I as defined in claim 1, wherein $R^2$ is a group (a).

14. A process as in claim 1 wherein the cation $X^+$ in the compound of formula IIIb is an ammonium, phosphonium, sulfonium, sulfoxonium, arsenium, alkali, earth alkali metal halogen, Zn(II)halogen or Cu(II)halogen cation.

15. A process as in claim 14, wherein $R^1$ is hydrogen.

16. A process as in claim 15 wherein $R^a$ and $R^b$ are acetyl.

* * * * *